(12) United States Patent
Federowicz et al.

(10) Patent No.: US 11,085,028 B2
(45) Date of Patent: Aug. 10, 2021

(54) APPARATUS FOR HARVESTING EGG FLUID, AND ASSOCIATED METHOD

(71) Applicant: ZOETIS SERVICES LLC, Parsippany, NJ (US)

(72) Inventors: Joseph Federowicz, Apex, NC (US); Louis Pallay, Ste-Anne-de-Bellevue (CA)

(73) Assignee: Zoetis Services LLC, Parsippany, NJ (US)

( * ) Notice: Subject to any disclaimer, the term of this patent is extended or adjusted under 35 U.S.C. 154(b) by 186 days.

(21) Appl. No.: 16/535,556

(22) Filed: Aug. 8, 2019

(65) Prior Publication Data

US 2019/0359950 A1    Nov. 28, 2019

Related U.S. Application Data

(62) Division of application No. 15/001,697, filed on Jan. 20, 2016, now Pat. No. 10,415,019.

(60) Provisional application No. 62/107,600, filed on Jan. 26, 2015.

(51) Int. Cl.
| | |
|---|---|
| *G01N 1/10* | (2006.01) |
| *C12N 7/00* | (2006.01) |
| *A01K 45/00* | (2006.01) |
| *C12M 3/10* | (2006.01) |
| *C12M 1/26* | (2006.01) |

(52) U.S. Cl.
CPC .............. *C12N 7/00* (2013.01); *A01K 45/007* (2013.01); *C12M 21/10* (2013.01); *C12M 33/04* (2013.01); *C12N 2760/16052* (2013.01)

(58) Field of Classification Search
CPC ............................ A01K 45/005; C12M 33/04
USPC ......................................... 436/177, 180, 174
See application file for complete search history.

(56) References Cited

U.S. PATENT DOCUMENTS

| | | | |
|---|---|---|---|
| 2,581,054 A | 1/1952 | Vansant | |
| 2005/0263079 A1* | 12/2005 | Karaca | ................. A01K 45/007 |
| | | | 119/6.8 |

FOREIGN PATENT DOCUMENTS

| | | |
|---|---|---|
| EP | 0 077 704 A1 | 4/1983 |
| JP | 2000-262272 A | 9/2000 |
| WO | WO 2013/138725 A2 | 9/2013 |

OTHER PUBLICATIONS

Japanese Patent Appln. No. 2017 533623, corres. to PCT/US2016/014215, Office Action, English Translation.

* cited by examiner

*Primary Examiner* — Natalia Levkovich
(74) *Attorney, Agent, or Firm* — Scott C. Mayhew (57) ABSTRACT

A harvesting apparatus adapted to harvest egg fluid from an avian egg is provided. Such an apparatus includes a frame. A harvesting assembly is operably engaged with the frame. The harvesting assembly includes a plurality of nozzles configured to remove egg fluid from an egg. The nozzles are configured to rotate from a vertically off-axis angled position toward a vertical position. A suction assembly is in fluid communication with the nozzles for harvesting egg fluid from an egg. An associated method is also provided.

8 Claims, 7 Drawing Sheets

APPARATUS FOR HARVESTING EGG FLUID, AND ASSOCIATED METHOD

CROSS REFERENCE TO RELATED APPLICATION

This application is a divisional of U.S. application Ser. No. 15/001,697, filed Jan. 20, 2016, which claims the benefit of U.S. Provisional Patent Application No. 62/107,600, filed Jan. 26, 2015, both of which are expressly incorporated herein by reference in their entirety.

TECHNICAL FIELD

The present disclosure generally relates to egg processing devices and systems. More particularly, the present disclosure relates to an apparatus for harvesting fluid from avian eggs, and an associated method.

BACKGROUND

Avian eggs may be used in the production of biologics such as viruses for vaccines, wherein such biologics must be harvested from the eggs at the appropriate time. One method of producing biologics is to use fertilized avian eggs. The desired biologics are grown within the egg and must be harvested therefrom for further processing. One method of producing vaccines, such as influenza vaccines, is to use fertilized avian (chicken) eggs. The eggs are injected with the viruses and, after a sufficient time of incubation to allow the virus to multiply, the eggs are opened or de-capped to harvest the viruses. Harvesting typically involves the collection of the allantoic fluid contained in the allantoic sac of a fertilized egg. The viruses are then separated from the fluid, purified, and inactivated to produce the final vaccine product.

Unfortunately, conventional harvesting systems and methods are not efficient in optimizing and maximizing fluid removal from the opened egg, in part due to the presence of the embryo within the egg. Such inefficiencies may lead to a loss in quantity of the final vaccine product produced.

Accordingly, it would be desirable to provide an apparatus capable of optimizing the fluid harvesting process and maximizing the volume of fluid removed from the egg. Furthermore, it would be desirable to provide an associated method to optimize the fluid harvesting process and maximize the volume of fluid removed from the egg.

BRIEF SUMMARY

The above and other needs are met by aspects of the present disclosure which, according to one aspect, provides a harvesting apparatus adapted to harvest egg fluid from an egg. The harvesting apparatus includes a frame and a harvesting assembly operably engaged with the frame. The harvesting assembly has a plurality of nozzles configured to remove egg fluid from an egg. The nozzles are configured to rotate from a vertically off-axis angled position toward a vertical position. A suction assembly is in fluid communication with the nozzles for harvesting egg fluid from an egg.

Another aspect provides a method of harvesting egg fluid from an avian egg. The method comprises providing a plurality of de-capped avian eggs to a harvesting apparatus comprising a harvesting assembly having a plurality of nozzles. The method further comprises positioning the avian eggs beneath the harvesting assembly such that each de-capped avian egg is positioned beneath a respective nozzle, each nozzle being angled vertically off-axis. The method further comprises positioning the nozzles within the de-capped avian eggs at an angle vertically off-axis. The method further comprises rotating the nozzles within the eggs toward a vertical position, and suctioning egg fluid from the de-capped avian through the nozzles.

Thus, various aspects of the present disclosure provide advantages, as otherwise detailed herein.

BRIEF DESCRIPTION OF THE DRAWINGS

Having thus described various embodiments of the present disclosure in general terms, reference will now be made to the accompanying drawings, which are not necessarily drawn to scale, and wherein:

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

Figure 1:
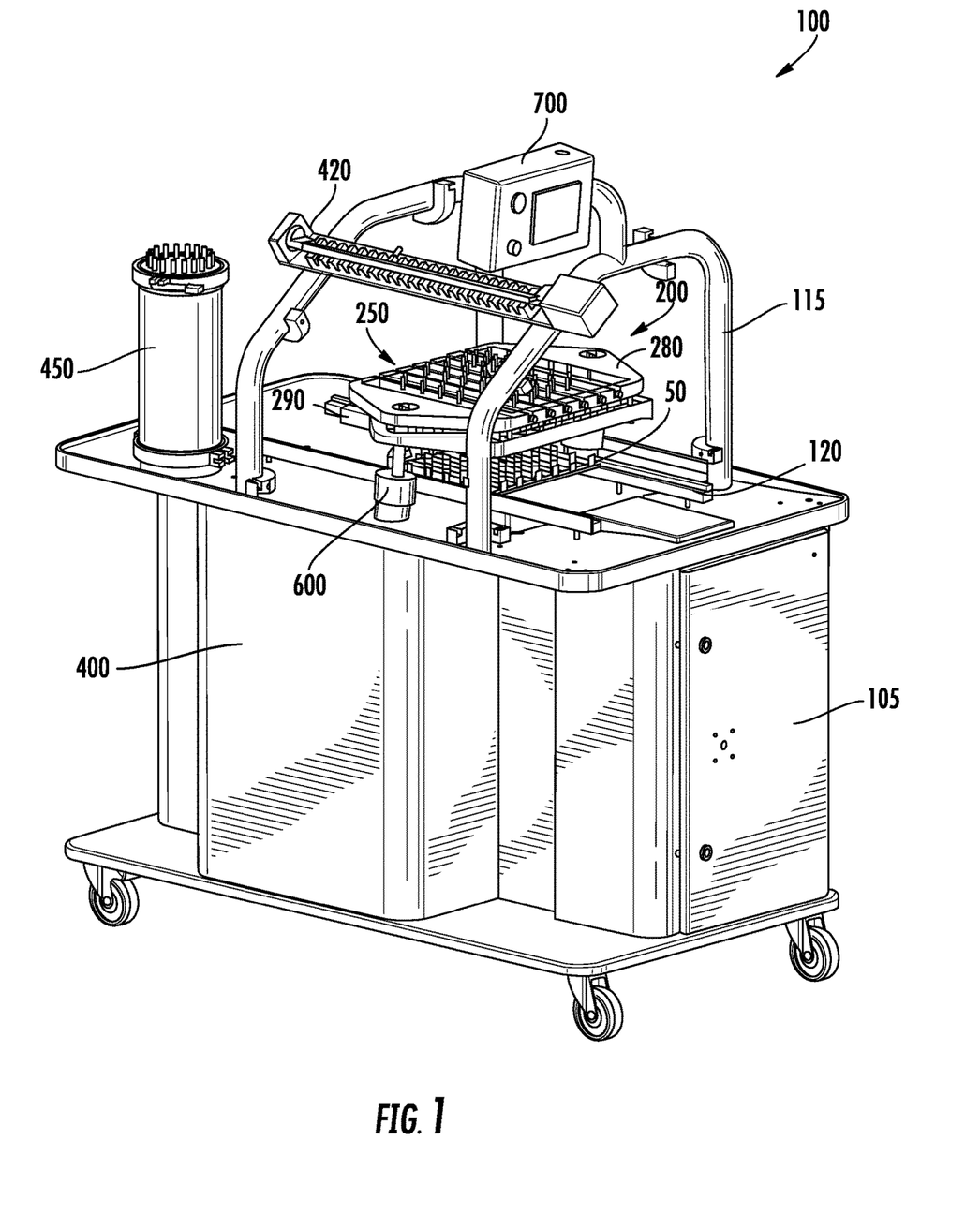
FIG. 1 is a front perspective view of a harvesting apparatus adapted to harvest egg fluid from a de-capped avian egg, according to one aspect of the present disclosure.
Figure 2:
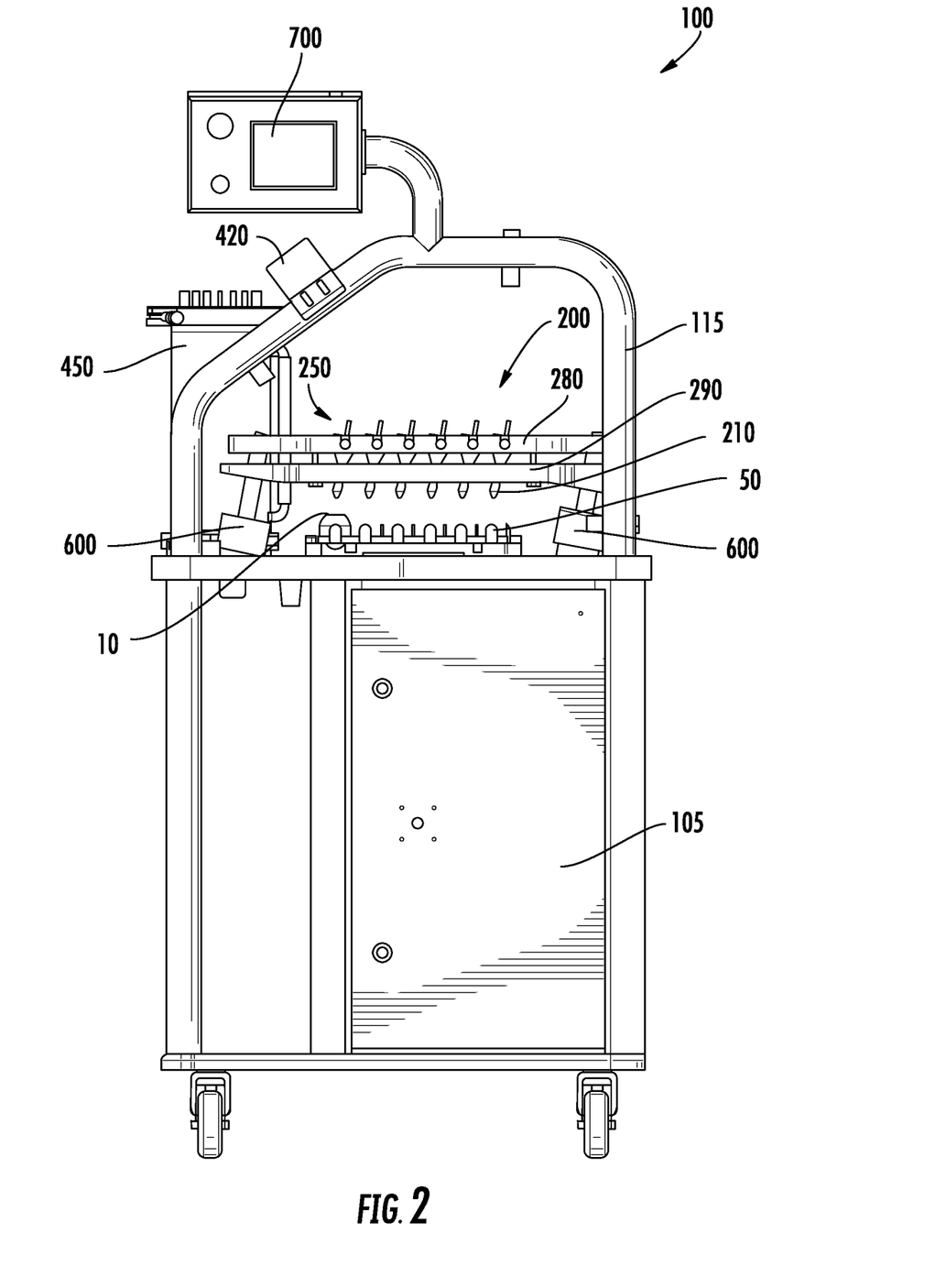
FIG. 2 is a side view of the harvesting apparatus of FIG. 1.

The apparatuses and methods of the present disclosure will now be described with reference to the figures. With initial reference to FIGS. 1 and 2, illustrated in the figures is an exemplary apparatus 100 for harvesting allantoic fluid from embryonated chicken eggs once the eggs are de-capped or otherwise have an opening created in the top portion of the egg shells. In some instances, a conveyor may be provided such that multiple eggs can be automatically received within the apparatus 100. An operator may manually loads trays 50 (so-called "flats") of de-capped eggs into the apparatus 100. Each tray 50 of de-capped eggs may then be moved through the apparatus 100 for processing at a harvesting assembly 200, wherein a desired fluid may be removed from the egg via a suction assembly 400. The eggs may then be directed or otherwise removed from the apparatus 100.

As mentioned previously, the de-capped eggs may be carried through the apparatus 100 on trays 50. Each tray 50 may be capable of holding a predetermined number of de-capped eggs in a matrix of individual egg support sections.

With further reference to FIGS. 1 and 2, trays 50 with de-capped eggs may be manually loaded onto a rail assembly 120. In some instances, the trays 50 may be placed onto a conveyor so as to create a continuous feed of trays 50. Any suitable tray loading means, manual or automated, and any suitable tray conveyor means may be used. Tray stops may be used to hold and release the trays 50 along the rail assembly 120 and/or conveyor to control the position of the trays 50 in the apparatus 100. Additional tray stops may be provided as needed to control the flow of trays 50 into and through the apparatus 100, and that each can be independently controlled with use of a sensor(s) to track the position of a tray 50.

The apparatus 100 may include a cart 105 having a frame 115 extending therefrom, wherein the cart 105 and/or the frame 115 may support the harvesting assembly 200. The conveyor may be configured to transport the trays 50 beneath the harvesting assembly 200.

Figure 3:
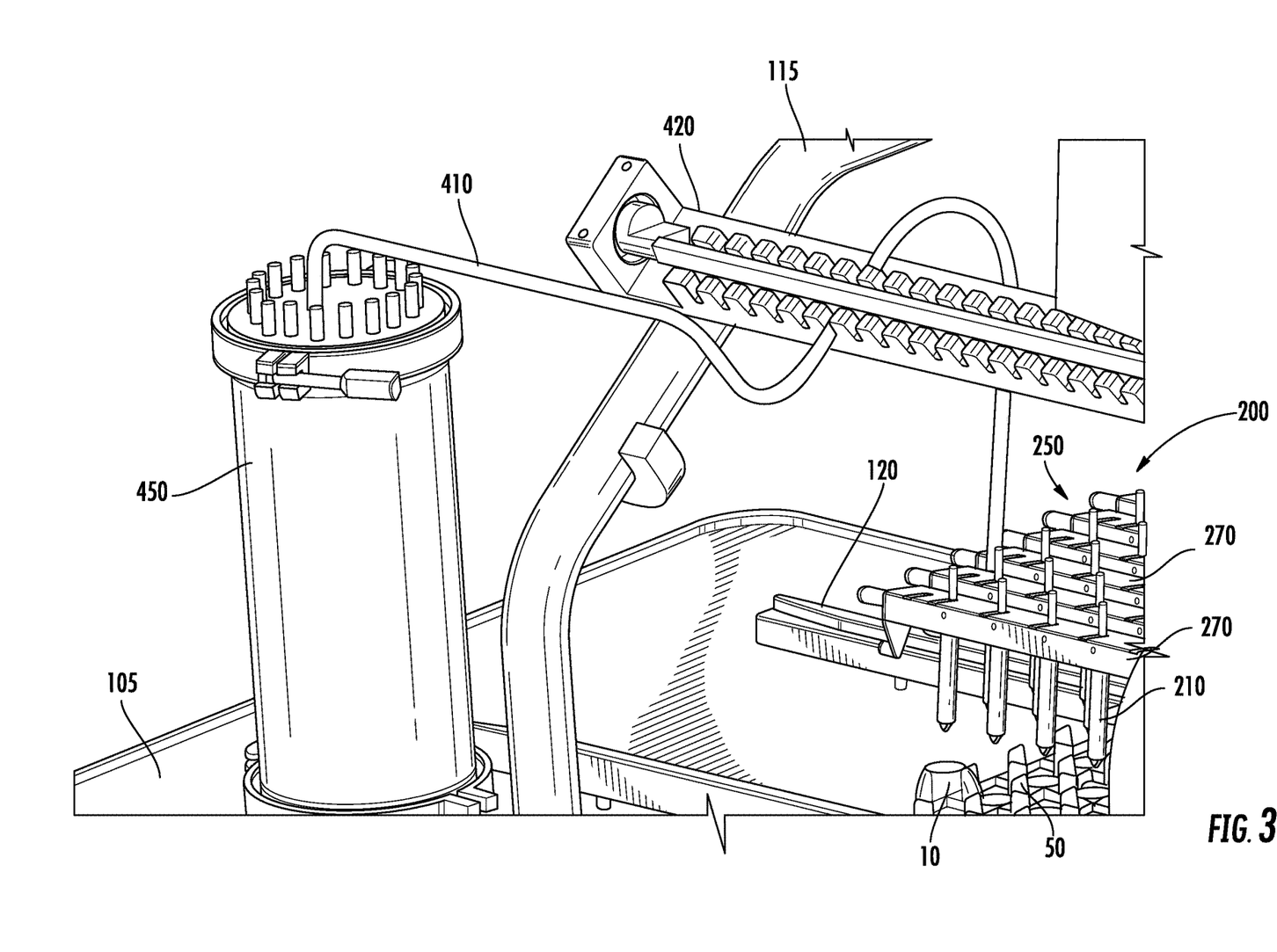
FIG. 3 is a magnified sectional view of the harvesting apparatus of FIG. 1, illustrating tubing connecting a fluid container and a nozzle, according to one aspect of the present disclosure.

As seen in FIGS. 1-3, the harvesting assembly 200 may include a plurality of nozzles 210 to be positioned within the eggs for removing the desired egg fluid therefrom. In this regard, the nozzles 210 may enter the de-capped eggs through the portion of the egg shell that has been removed. The nozzles 210 may be in fluid communication with a suction assembly 400 that applies vacuum to draw or otherwise remove egg fluid from the egg. Each nozzle 210 may be connected to a fluid container 450 via tubing 410, as shown in FIG. 3 (only one tubing 410 shown for clarity). The egg fluid may move from the nozzle 210 through the tubing 410 and into the fluid container 450 where the egg fluid is collected. The fluid container 450 may be removed or accessed as needed to remove the collected egg fluid. Each tubing 410 may run through a line separator 420 to separate and maintain position of the tubing 410.

Figure 4:
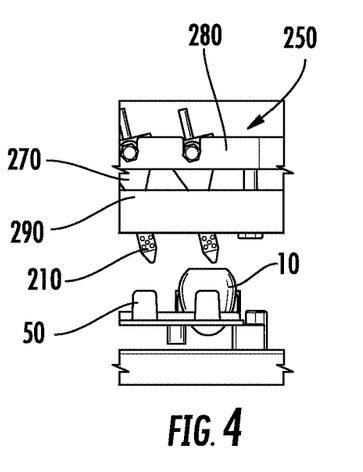
FIGS. 4-9 are magnified sectional views of the harvesting apparatus of FIG. 1, illustrating rotation of a nozzle within a de-capped avian egg, according to one aspect of the present disclosure.
Figure 5:
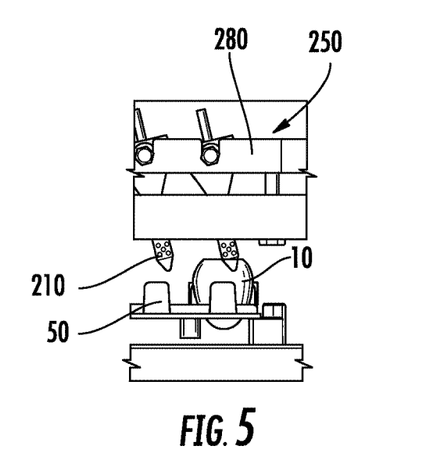
Figure 6:
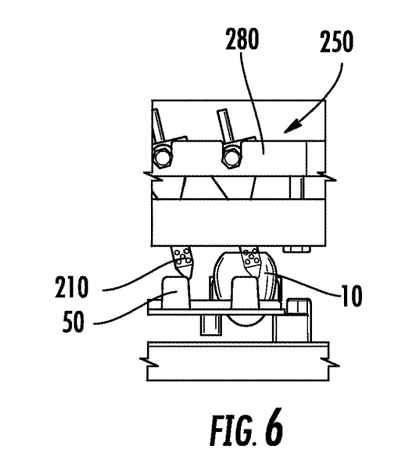
Figure 7:
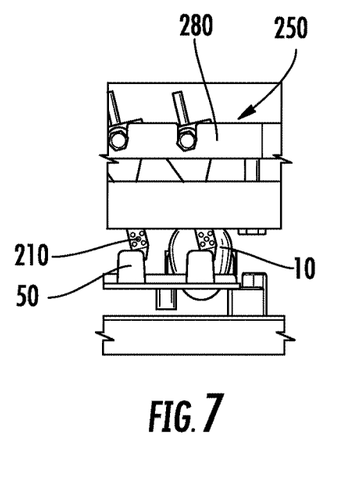
Figure 8:
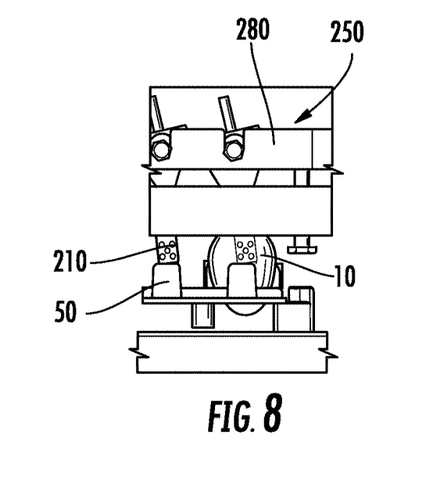
Figure 9:
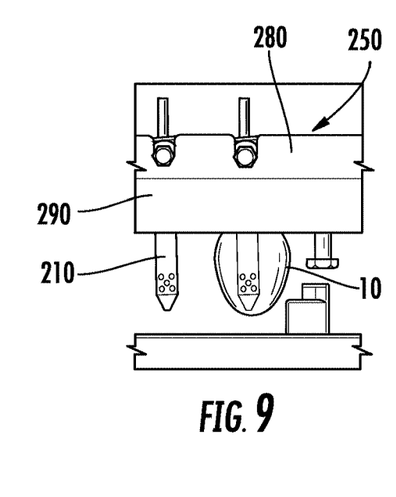
Figure 10:
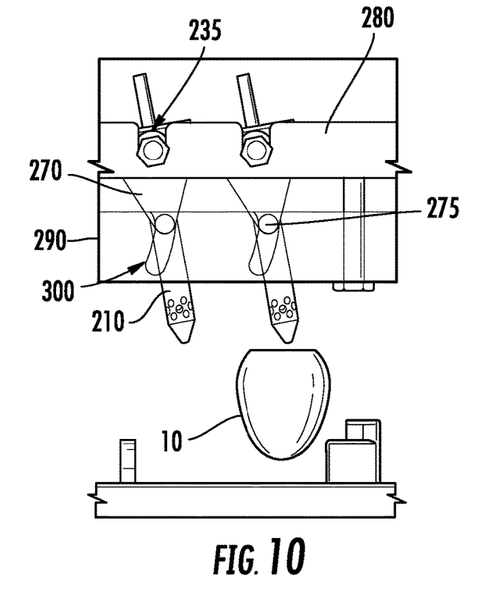
FIGS. 10-13 are magnified sectional views of the harvesting apparatus of FIG. 1, illustrating rotation of a nozzle within a de-capped avian egg via use of an arcuate guideway, according to one aspect of the present disclosure.
Figure 11:
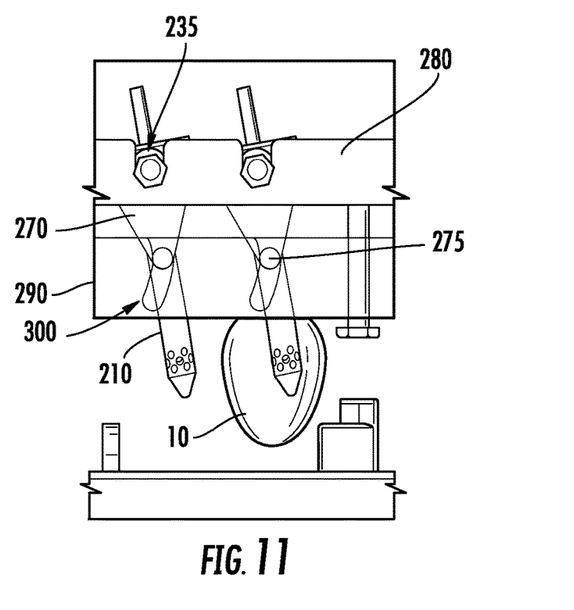

With reference to FIGS. 4-9, the harvesting assembly 200 is now described. According to aspects of the present disclosure, the nozzles 210 of the harvesting assembly 200 may be capable of rotating, sweeping, or otherwise moving within an egg 10 so as to improve the egg fluid removal process. In this regard, the nozzle 210 may be angled with respect to vertical upon entry and positioning within the egg 10, as shown in FIGS. 4 and 5. By angling the nozzle 210 toward the side of the egg 10, the embryo within the egg 10 may be avoided as the nozzle 210 is positioned within the egg 10. In this regard, the embryo may be generally centrally located within the egg 10, so entering the nozzle within the egg completely vertical may cause the nozzle to interfere with the embryo, thereby affecting the amount of desired egg fluid that can be removed. Accordingly, aspects of the present disclosure aim to avoid interference with the embryo by entering the egg 10 at an angle, wherein the nozzle 210 may then be rotated or moved in a sweeping motion toward a vertical position such that the nozzle 210 removes egg fluid from the bottom of the egg 10, as shown in FIG. 9 (a portion of the tray 50 moved for clarity). In this manner, the nozzle 210 may be used to move the embryo to the side of the egg 10 and out of the way. FIGS. 4-9 illustrate the sequence in which the nozzle 210 enters the egg 10 at an angle from vertical and then is rotated to a substantially vertical position. In this regard, the nozzles 210 may be configured to articulate by rotating from a vertically off-axis angled position toward a vertical position.

The nozzles 210 may be angled at various angles with respect to vertical upon positioning within the egg 10. For example, the nozzles 210 may be angled at between about 8 degrees and about 12 degrees from a vertical direction and preferably at about 10 degrees from vertical.

The nozzles 210 may be rotated in any manner. According to one aspect, as shown in FIGS. 10-15, the harvesting assembly 200 may include a nozzle holder assembly 250 having a plurality of nozzle holders 270 to which the nozzles 210 are connected. The nozzle holders 270 may be engaged with and freely rotatable with respect to a nozzle holder frame 280 such that the nozzles 210 are capable of corresponding rotation with the nozzle holders 270. In this regard, the nozzle holders 270 may include cylindrical projections 230 on either end thereof, which may be received within a slot 235 of the nozzle holder frame 280 (removed in FIG. 14 for clarity). The nozzle holders 270 may hang freely within the slots 235 such that the nozzle holders 270 are freely rotatable.

The harvesting assembly 200 may include a stationary guide frame 290 defining a plurality of guideways 300. Each nozzle holder 270 may include laterally extending portions 275 projecting from opposing ends 271, 272 thereof and configured to operate in the guideways 300. According to one particular aspect, the guideways 300 may be arcuate grooves configured to facilitate rotational movement of the nozzle holders 270 (and thus the nozzles 210) as the nozzle holder assembly 250 descends and ascends. While the illustrated aspects are described in a manner in which the trays 50 and eggs remain stationary while the nozzles 210 are lowered, it will be noted that in some instances the nozzles 210 could remain stationary while the trays 50 and eggs are raised to the nozzles 210, prior to rotation of the nozzles 210. The harvesting assembly may include one or more actuators 600 for moving the nozzle holder assembly 250 (and particularly the nozzle holder frame 280) vertically so as to facilitate rotation of the nozzle holders 270 and nozzles 210. To that end, movement of the laterally extending portions 275 within the guideways 300 as the nozzle holder assembly 250 descends or ascends causes the nozzle holders 270, and hence the nozzles 210, to rotate or otherwise move in a sweeping motion.

Figure 12:
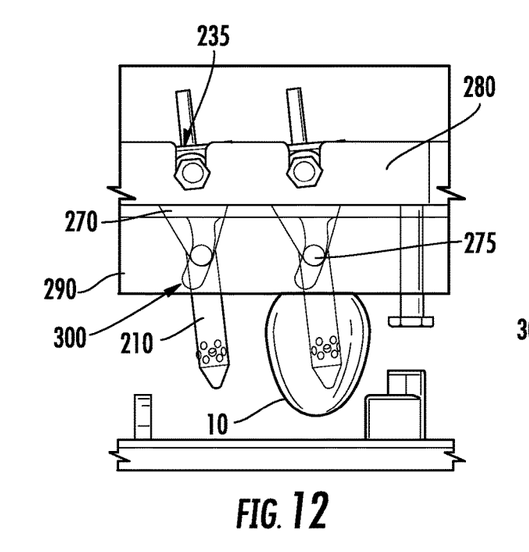
Figure 13:
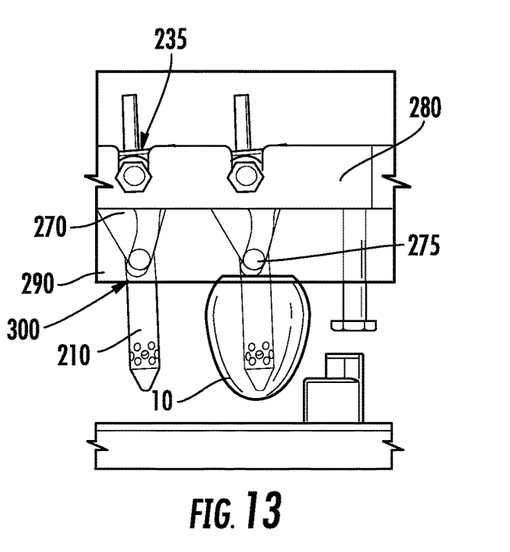
Figure 14:
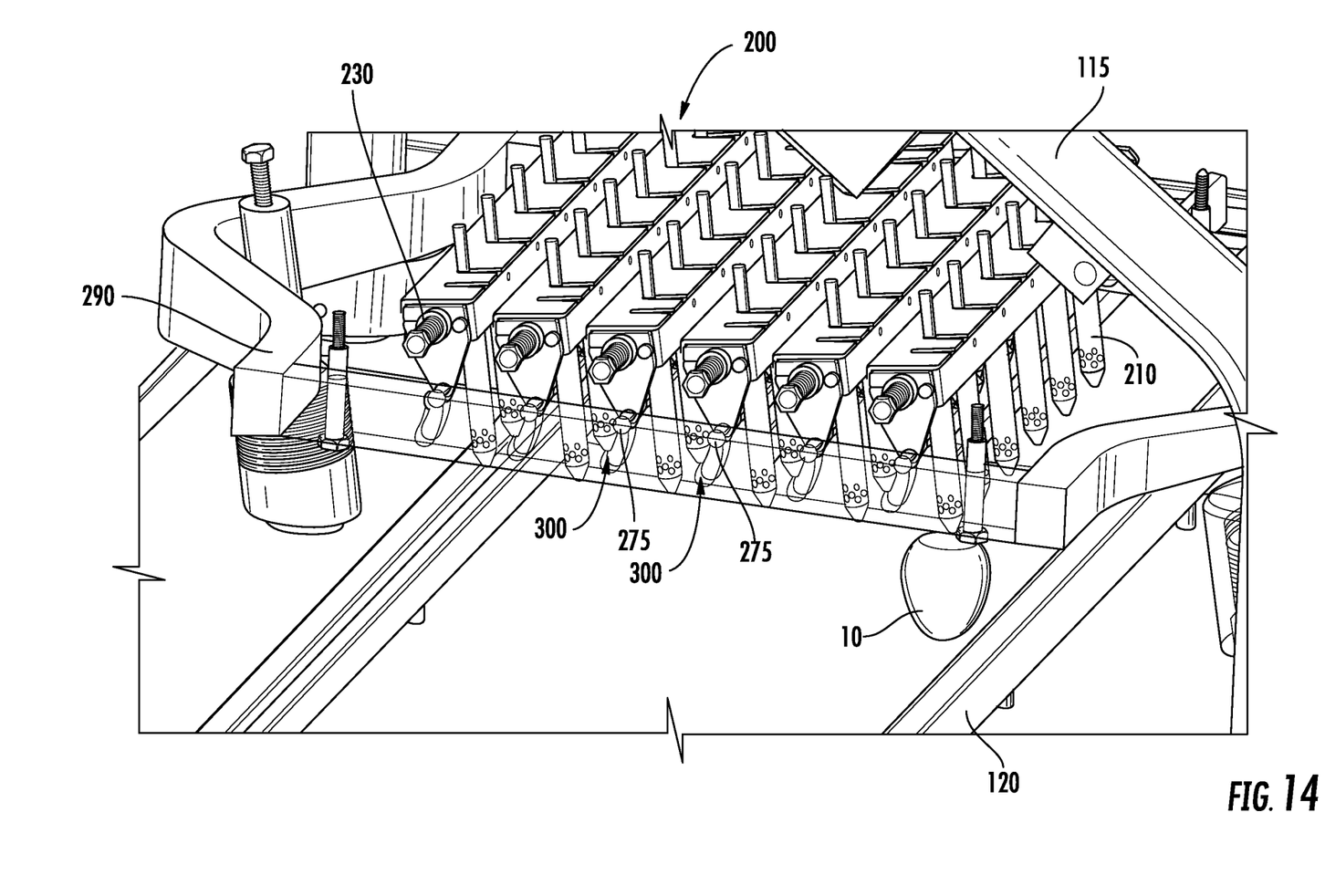
FIG. 14 is a is a magnified sectional view of the harvesting apparatus of FIG. 1, illustrating a harvesting assembly having a plurality of nozzle holders and nozzles, according to one aspect of the present disclosure.
Figure 15:
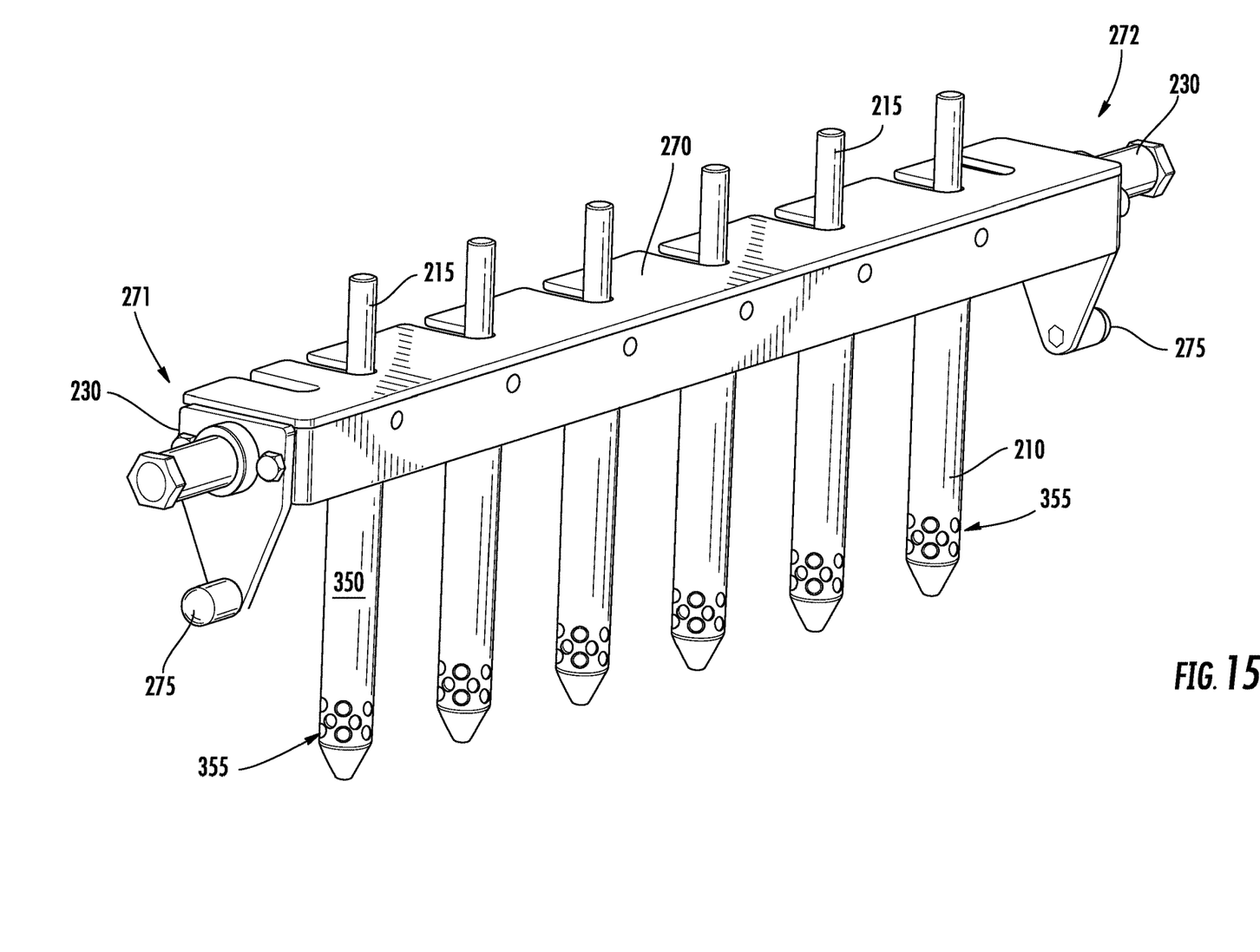
FIG. 15 is a perspective view of a nozzle holder having a plurality of nozzles operably engaged therewith, according to one aspect of the present disclosure.

In some instances, one of the actuators 600 may be used to move the entire harvesting assembly 200 (i.e., the stationary guide frame 290 and the nozzle holder assembly 250) vertically so as to move the harvesting assembly 200 proximate to the de-capped eggs, as shown in FIGS. 4-7, 10 and 11. In this regard, the stationary guide frame 290 and the nozzle holder assembly 250 may be connected to one or more extension rods that facilitate vertical movement of the stationary guide frame 290 and the nozzle holder assembly 250. In this sense, the term "stationary" the stationary guide frame 290 refers to the inactive state or stationary position of the stationary guide frame 290 during the process when the nozzle holder assembly 250 is vertically lowered with respect to the stationary guide frame 290 such that the gap between the frames thereof is eliminated and the frames of the stationary guide frame 290 and the nozzle holder assembly 250 are in contact, as shown in FIGS. 9 and 13. By the stationary guide frame 290 remaining stationary once lowered proximate to the eggs, the laterally extending portions 275 may be moved through the guideways 300 so as to articulate the nozzles 210, as shown in FIGS. 8 and 12. In some instances, a second actuator 600 may be used to move the nozzle holder assembly 250 relative to the stationary guide frame 290 such that the nozzles 210 are rotated within the eggs. That is, the relative motion between the stationary guide frame 290 and the nozzle holder assembly 250 causes the nozzles to rotate within the egg. However, in order for eggs to be moved beneath the harvesting assembly 200 the stationary guide frame 290 and the nozzle holder assembly 250 may be capable of concurrent movement so as to be raised and lowered together for at least some distance. In some instances, movement of the stationary guide frame 290 in a downward direction may be halted by some physical structure or impediment such that the stationary guide frame 290 becomes stationary, thereby allowing for the relative motion of the nozzle holder assembly 250 with respect to the stationary guide frame 290.

The nozzles 210 may have a cylindrical body 350 defining a plurality of holes 355 through which egg fluid enters an interior of the nozzle 210 during removal of egg fluid from the egg. The end of the nozzles 210 may be frustoconically shaped. The nozzles 210 may include a stem 215 for receiving the tubing 410.

The actuators 600 may be of any suitable type mechanism. For example, the actuators 600 may be an air cylinder type actuator, among others.

Sensors, controllers, and other electronics as known in the art can be used to control the movements and processes of the apparatus 100. The apparatus 100 may include a human machine interface (HMI) 700 for housing a controller to control the apparatus 100 and providing an interface for inputting processing protocols or parameters by the user.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A method of harvesting egg fluid from an avian egg, the method comprising:
   providing a plurality of de-capped avian eggs to a harvesting apparatus comprising a harvesting assembly having a plurality of nozzles;
   positioning the avian eggs beneath the harvesting assembly such that each de-capped avian egg is positioned beneath a respective nozzle, each nozzle being angled vertically off-axis;
   positioning the nozzles within the de-capped avian eggs at an angle vertically off-axis;
   rotating the nozzles within the eggs toward a vertical position; and
   suctioning egg fluid from the de-capped avian through the nozzles.

2. A method according to claim 1, wherein the nozzles are angled vertically off-axis at between about 8 degrees and about 12 degrees.

3. A method according to claim 1, wherein the harvesting assembly comprises a nozzle holder assembly having a plurality of nozzle holders with which the nozzles are operably engaged, the nozzle holders being operably engaged with and freely rotatable with respect to a nozzle holder frame such that the nozzles are capable of corresponding rotation with the nozzle holders.

4. A method according to claim 3, wherein the harvesting assembly includes a stationary guide frame defining a plurality of guideways, and further wherein the nozzle holders each include laterally extending portions projecting from opposing ends thereof and configured to operate in the guideways.

5. A method according to claim 4, wherein the guideways comprise arcuate grooves configured to facilitate rotational movement of the nozzle holders and nozzles as the nozzle holder assembly descends and ascends.

6. A method according to claim 4, further comprising an actuator configured to move the nozzle holder assembly vertically so as to facilitate rotation of the nozzle holders and nozzles.

7. A method according to claim 1, wherein the nozzles each have a cylindrical body defining a plurality of holes through which egg fluid enters an interior of the nozzle during removal of egg fluid from an egg.

8. A method according to claim 1, wherein positioning the nozzles within the de-capped avian eggs at an angle vertically off-axis comprises lowering the nozzles to enter the de-capped avian eggs at an angle vertically off-axis.

* * * * *